US012774918B2

(12) United States Patent
Kim et al.

(10) Patent No.: US 12,774,918 B2
(45) Date of Patent: Oct. 27, 2026

(54) FREQUENCY-SELECTIVE SIGNAL DAMPER CONTAINING GELATIN AND CHITOSAN HYDROGEL, AND A DEVICE MEASURING SIGNAL USING THE SAME

(71) Applicant: RESEARCH & BUSINESS FOUNDATION SUNGKYUNKWAN UNIVERSITY, Suwon-si (KR)

(72) Inventors: Tae Il Kim, Suwon-si (KR); Byeong Hak Park, Suwon-si (KR); Su Bin Park, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 1110 days.

(21) Appl. No.: 17/742,881

(22) Filed: May 12, 2022

(65) Prior Publication Data

US 2022/0364910 A1 Nov. 17, 2022

(30) Foreign Application Priority Data

May 12, 2021 (KR) ........................ 10-2021-0061065

(51) Int. Cl.

| | |
|---|---|
| ***G01H 11/06*** | (2006.01) |
| ***A61B 5/00*** | (2006.01) |
| ***A61B 5/024*** | (2006.01) |
| ***A61B 5/279*** | (2021.01) |
| ***A61B 5/28*** | (2021.01) |
| ***A61B 5/291*** | (2021.01) |

(52) U.S. Cl.

CPC ......... *G01H 11/06* (2013.01); *A61B 5/02438* (2013.01); *A61B 5/279* (2021.01); *A61B 5/28* (2021.01); *A61B 5/291* (2021.01); *A61B 5/6833* (2013.01); *A61B 5/7207* (2013.01)

(58) Field of Classification Search

CPC ................................ G01H 11/06; A61B 5/279

See application file for complete search history.

(56) References Cited

U.S. PATENT DOCUMENTS 9,927,311 B2 * 3/2018 Kang .................... H05K 1/167

FOREIGN PATENT DOCUMENTS

CN 111956868 A * 11/2020 ............. A61L 27/56
KR 10-2018-0097969 A 9/2018

OTHER PUBLICATIONS

English machine translation Yan et al. (CN 111956868) (Year: 2020).*

Cacopardo, Ludovica, et al. "Engineering hydrogel viscoelasticity." Journal of the mechanical behavior of biomedical materials 89 (2019): 162-167.

Shabaniverki, Soheila, et al. "Characterizing gelatin hydrogel viscoelasticity with diffusing colloidal probe microscopy." Journal of colloid and interface science 497 (2017): 73-82.

Zhu, Longxiang, et al. "A high modulus hydrogel obtained from hydrogen bond reconstruction and its application in vibration damper." RSC advances 7 (2017): 43755-43763.

* cited by examiner

*Primary Examiner* — Michael F Pepitone
(74) *Attorney, Agent, or Firm* — NSIP Law

(57) ABSTRACT

Disclosed is a frequency-selective signal damper including: a viscous polymer exhibiting non-Newtonian fluid behavior; and hydrogel exhibiting sol-gel phase transition. The viscous polymer exhibits shear thinning in a damping region or a noise region, and the hydrogel has a sol phase in the damping region or the noise region. The viscous polymer is gelatin, and the hydrogel is chitosan.

17 Claims, 8 Drawing Sheets

FREQUENCY-SELECTIVE SIGNAL DAMPER CONTAINING GELATIN AND CHITOSAN HYDROGEL, AND A DEVICE MEASURING SIGNAL USING THE SAME

CROSS-REFERENCE TO RELATED APPLICATION

This application claims a benefit under 35 U.S.C. § 119(a) of Korean Patent Application No. 10-2021-0061065 filed on May 12, 2021, in the Korean Intellectual Property Office, the entire disclosure of which is incorporated herein by reference for all purposes.

BACKGROUND

1. Field

The present disclosure relates to a frequency-selective signal damper based on gelatin and hydrogel of chitosan and an application using the same.

2. Description of Related Art

In a prior art, for selective damping and sensing of a signal of an electronic device, there have been attempts to directly absorb sound with a material or to perform signal processing.

The selective damping has been performed using a porous material. In this scheme, energy loss of reflected signal therefrom, or resonance therein is used. However, the porous material absorbs a very high frequency sound (>1,000 Hz or greater). Thus, at low frequencies, damping performance is low or selective sound absorption is not achieved, and a damping frequency band is not adjusted.

In particular, for example, when using a commercial product such as alpha gel, D3O for reducing shock absorption, a low frequency sound absorption is targeted, and a natural frequency of a material is targeted to absorb sound and adjust viscous property. However, in this case, 1) it is impossible to set a bandwidth, 2) it is difficult to exhibit a high sound absorption rate in which a difference between a sound absorption zone and a transmission zone is 3 times larger, and 3) it is very difficult to actively control the bandwidth. It is difficult to have a dramatic transition at room temperature because a glass transition temperature of an existing polymer material is below the room temperature. In addition, when using a shear thickening polymer, there is a disadvantage in that change is not made dramatically.

The signal processing may include a method using wave interference such as noise cancellation, or a post-processing method of removing a detected signal using a signal processing algorithm such as machine learning or deep learning. However, this requires complex hardware electronic circuits or a software process based on a larger amount of database. This requires unnecessary devices and software.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide a material capable of selective damping based on material properties that may remove the existing disadvantage of being unable to selectively damp a physical signal or of requiring the very complex circuit or the software process based on the larger amount of database.

Purposes in accordance with the present disclosure are not limited to the above-mentioned purpose. Other purposes and advantages in accordance with the present disclosure as not mentioned above may be understood from following descriptions and more clearly understood from embodiments in accordance with the present disclosure. Further, it will be readily appreciated that the purposes and advantages in accordance with the present disclosure may be realized by features and combinations thereof as disclosed in the claims.

A first aspect of the present disclosure provides a frequency-selective signal damper comprising: a viscous polymer exhibiting non-Newtonian fluid behavior; and hydrogel exhibiting sol-gel phase transition. In particular, when the viscous polymer exhibits shear thickening properties and the hydrogel has a sol phase, in the region where the signal is selectively damped, that is, the noise region, the slope (selectivity) of the tangent delta value based on the frequency in this region is high, thereby selectively damping the frequency signal.

In one implementation of the frequency-selective signal damper, the viscous polymer exhibits shear thinning in a damping region or a noise region, wherein the hydrogel has a sol phase in the damping region or the noise region.

In one implementation of the frequency-selective signal damper, the viscous polymer has a Deborah number of 1 or lower in a damping region or a noise region.

In one implementation of the frequency-selective signal damper, the viscous polymer is gelatin, and the hydrogel is chitosan.

The frequency-selective signal damper means a material that damps or absorbs a specific region of a frequency signal such as vibration or electrical signal, and passes therethrough a signal in a remaining region.

In one implementation of the frequency-selective signal damper, the signal is a physical or electromagnetic signal. The signal to be measured may be a physical or electrical signal. The physical signal may be a signal according to vibration or impact. For example, acoustic signals, heart rate, and pulse may be examples of physical signals. The electrical signal may be an EEG, and an electrocardiogram.

In one implementation of the frequency-selective signal damper, in a damping frequency band (50 Hz or lower), the damper has a tangent delta value based on a frequency in a range of 4 or greater.

The tangent delta value based on the frequency refers to the slope of the tangent delta value based on frequency, and is referred to as the selectivity in the present disclosure. The damper according to the present disclosure exhibits a high tangent delta value under a small frequency change, which means that the damper exhibits high frequency selectivity before and after the damping frequency. That is, the damper exhibits higher selectivity when signals with two different frequencies are input thereto. Compared to other hydrogels or viscoelastic materials that usually exhibit a value of 3 or lower of the selectivity, the hydrogel according to the present disclosure is characterized by exhibiting a selectivity value of up to 15, and thus may act as a selective frequency signal damper exhibiting excellent performance In one implementation of the frequency-selective signal damper, a content of the gelatin is in a range of 20 to 500 parts by weight based on 100 parts by weight of the chitosan.

In the composition ratio in this range, the damper in accordance with the present disclosure exhibit high selectivity values of larger than 5.

In one implementation of the frequency-selective signal damper, the damper selectively damps a physical signal having a frequency below or equal to 50 Hz at a temperature below 50 degrees C. In particular, at room temperature (25 degrees), a physical signal of 1 Hz or less is selectively damped.

The damper according to the present disclosure may damp a signal of a low frequency band such as a human movement, and thus remove a noise signal according to a human movement from a device measuring a bio-signal, thereby increasing the measurement quality of a measurement target frequency.

A second aspect of the present disclosure provides an electrode for measuring a bio-signal, wherein electrode includes the frequency-selective signal damper.

In one implementation of the electrode, the bio-signal includes a heart rate, brainwave, electrocardiogram, pulse or voice.

A third aspect of the present disclosure provides a signal discrimination sensor including the frequency-selective signal damper as defined above.

In one implementation of the sensor, the signal discrimination sensor is a pass filter or a stop filter.

A fourth aspect of the present disclosure provides a vibration measuring device comprising: a vibration measuring sensor; and the frequency-selective signal damper stacked on one face or each of both opposing faces of the measurement sensor.

In one implementation of the device, the vibration measuring sensor includes: a support; and a conductive thin metal film formed on at least one side of the support, wherein the conductive thin film includes cracks that are artificially formed according to an orientation direction, at least some of which have opposing surfaces in partial contact with each other, the crack surfaces undergo a variation in contact area or disconnection-reconnection events to cause a change in electrical resistance while moving relative to each other in response to external physical stimuli, and the sensor detects the resistance change to measure the external stimuli.

Effects in accordance with the present disclosure may be as follows but may not be limited thereto.

The present disclosure provides a frequency-selective damping material with a very high selectivity in a damping band and a high signal-to-noise ratio.

In addition to the effects as described above, specific effects in accordance with the present disclosure will be described together with the detailed description for carrying out the disclosure.

DETAILED DESCRIPTIONS

Figure 1:
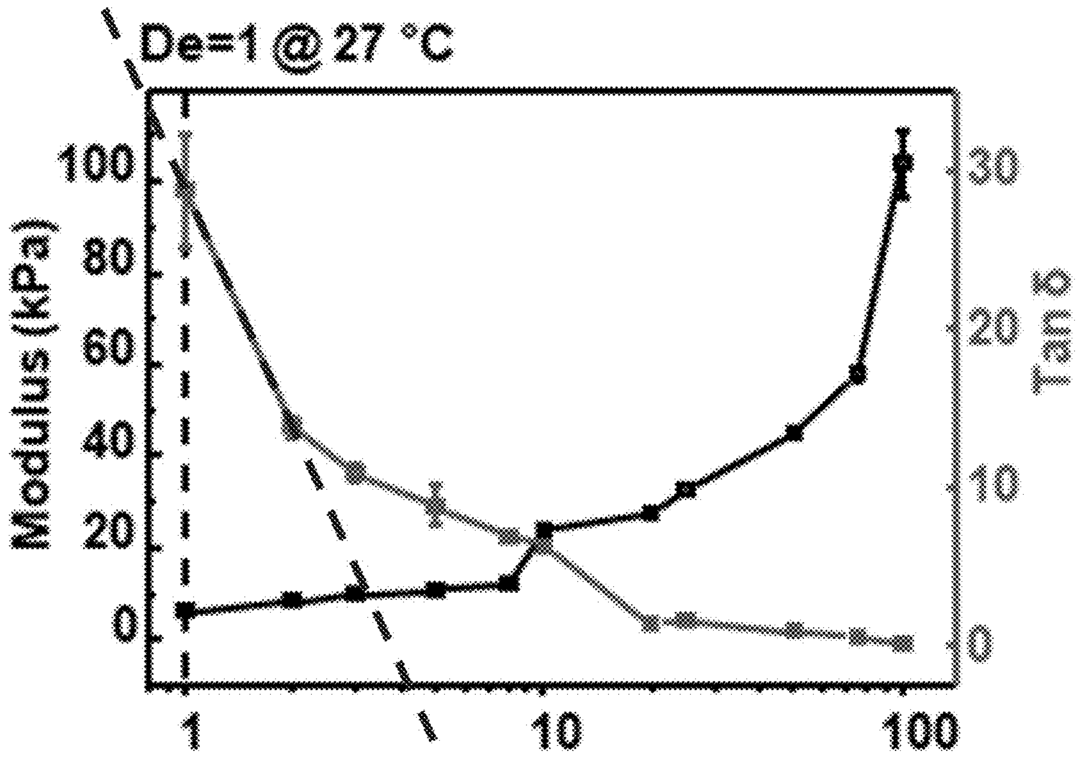
FIG. 1 is an example of a graph to illustrate calculation of a selectivity as a slope of a tangent delta value based on a frequency according to the present disclosure.

For simplicity and clarity of illustration, elements in the drawings are not necessarily drawn to scale. The same reference numbers in different drawings represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure. Examples of various embodiments are illustrated and described further below. It will be understood that the description herein is not intended to limit the claims to the specific embodiments described. On the contrary, it is intended to cover alternatives, modifications, and equivalents as may be contained within the spirit and scope of the present disclosure as defined by the appended claims.

A shape, a size, a ratio, an angle, a number, etc. disclosed in the drawings for illustrating embodiments of the present disclosure are illustrative, and the present disclosure is not limited thereto. The same reference numerals refer to the same elements herein. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entirety of list of elements and may not modify the individual elements of the list. When referring to "C to D", this means C inclusive to D inclusive unless otherwise specified.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The hydrogel according to the present disclosure exhibits a sol-gel transition depending on a frequency band and contains a polymer that exhibits non-Newtonian fluid behavior. For example, the hydrogel exhibiting the sol-gel transition is gelatin, and the polymer exhibiting the non-Newtonian fluid behavior is chitosan.

The hydrogel according to the present disclosure is capable of selective damping while removing the existing disadvantage of being unable to selectively damp a physical signal or of requiring the very complex circuit or the software process based on the larger amount of database.

The selective damping of the hydrogel according to the present disclosure is based on the properties that damping varies depending on the frequency of the physical vibration signal, based on shear thickening and shear thinning as the non-Newtonian behavior. In the noise band (50 Hz or below), chitosan exhibits shear thickening. The gelatin exhibits a phase transition from sol to gel in the signal band (50 Hz or greater). Thus, the damping based on the shear thickening and the sol phase may occur in the noise band (50 Hz or lower), while in the signal band, signal transmission based on the shear thinning and the gel phase may occur.

The hydrogel according to the present disclosure has the advantage of controlling the damping width by controlling the temperature. In particular, based on the shear-thickening, the damping may occur at a relatively high frequency, while based on the shear-thinning, the transmission may occur at a relatively high frequency.

The present disclosure achieves the selective signal damping using viscoelastic properties and hydrogel transition properties from a material point of view. The viscoelastic property is a mechanical property with respect to time. Thus, among time elements that may define the same, a relaxation time which is the time for stress recovery determines a width of the damping band, and a tangent delta as a ratio between a storage modulus and a loss modulus determines the width of the damping. The Deborah number may be defined as the ratio of the time corresponding to a period of external vibration and the relaxation time. Based on whether the Deborah number is smaller than or greater than 1, it may be determined whether the material is macroscopically viscous or elastic. That is, the Deborah number may be viewed as a measure for determining whether the damping occurs or not. When the selectivity is high, the sound absorption characteristics at the frequency at which damping occurs and the frequency at which damping does not occur based on the Deborah number of 1 are different from each other. Thus, when the selectivity is high, the damping may clearly occur at a specific frequency.

In addition, the damping band may change abruptly as the relaxation time changes abruptly based on a temperature. The high diffusion coefficient of the chains of the hydrogel may impart a high diffusion coefficient to the hydrogel according to the present disclosure. This is considered to induce the rapid change in the relaxation time based on the frequency or the temperature.

Hereinafter, various Examples and Experimental Examples according to the present disclosure will be described in detail. However, the following Examples are merely some embodiments of the present disclosure, and the present disclosure should not be construed as being limited to the following Examples.

The gelatin/chitosan hydrogel according to the present disclosure was prepared.

Example 1

Chitosan powders (Sigma-Aldrich) were dissolved in a 2 wt % acetic acid solution (Samchun) for one day to prepare a 4 wt % chitosan solution. An internal pH of the solution was adjusted to 5 to with sodium hydroxide solution.

A 10 wt % gelatin solution was prepared using gelatin from pig skin (G2500; Sigma-Aldrich) and deionized water.

The two solutions were mixed with each other at a mass ratio of gelatin to chitosan of 2:1, and a concentration of the mixed solution was adjusted to 5% by weight with additional distilled water, and the mixed solution was stirred at 50° C. for 3 hours.

Example 2

A hydrogel according to the present disclosure was prepared in the same manner as in the method of Example 1 except for a ratio of gelatin to chitosan of 5:1.

Example 3

A hydrogel according to the present disclosure was prepared in the same manner as in the method of Example 1 except for a ratio of gelatin to chitosan of 1:5 (0.2:1).

Hereinafter, the excellent characteristics of the hydrogel according to the present disclosure will be described with reference to comparison between the selectivity values of the hydrogel according to the present disclosure as prepared in the above examples and other hydrogels and viscoelastic materials as controls.

Selectivity is defined as the tangent delta value based on the frequency. Selectivity is defined as a slope of the tangent delta value based on the frequency. The tangent delta value based on the frequency stimulus is measured using a dynamic mechanical analysis (DMA) device. Thus, a slope based on the frequency is calculated as shown in FIG. 1.

Figure 2:
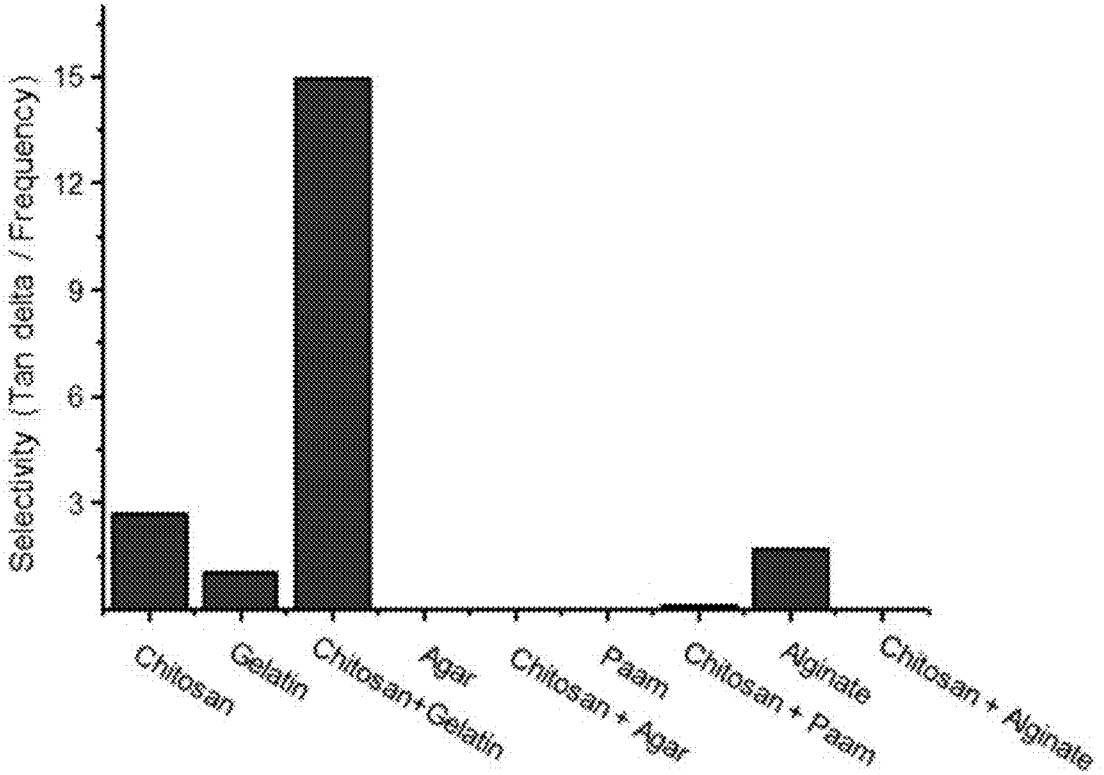
FIG. 2 is a bar graph of selectivity values in a damping frequency band of each of hydrogel (Chitosan+Gelatin) of Example 1 of the present disclosure, and other materials

FIG. 2 is a bar graph of selectivity values in the damping frequency band of each of the hydrogel (Chitosan+Gelatin) of Example 1 of the present disclosure and other materials. The hydrogel of Example 1 has superior values compared to other hydrogels and viscoelastic materials. This indicates that the hydrogel of Example 1 has many viscous bonds (i.e. hydrogen bonds) therein, and has the rapid change in the relaxation time due to the mobility of water, thus at the same time exhibiting high energy absorption and high selectivity. Thus, the hydrogel of Example 1 may act as a damper exhibiting excellent performance.

Figure 3A:
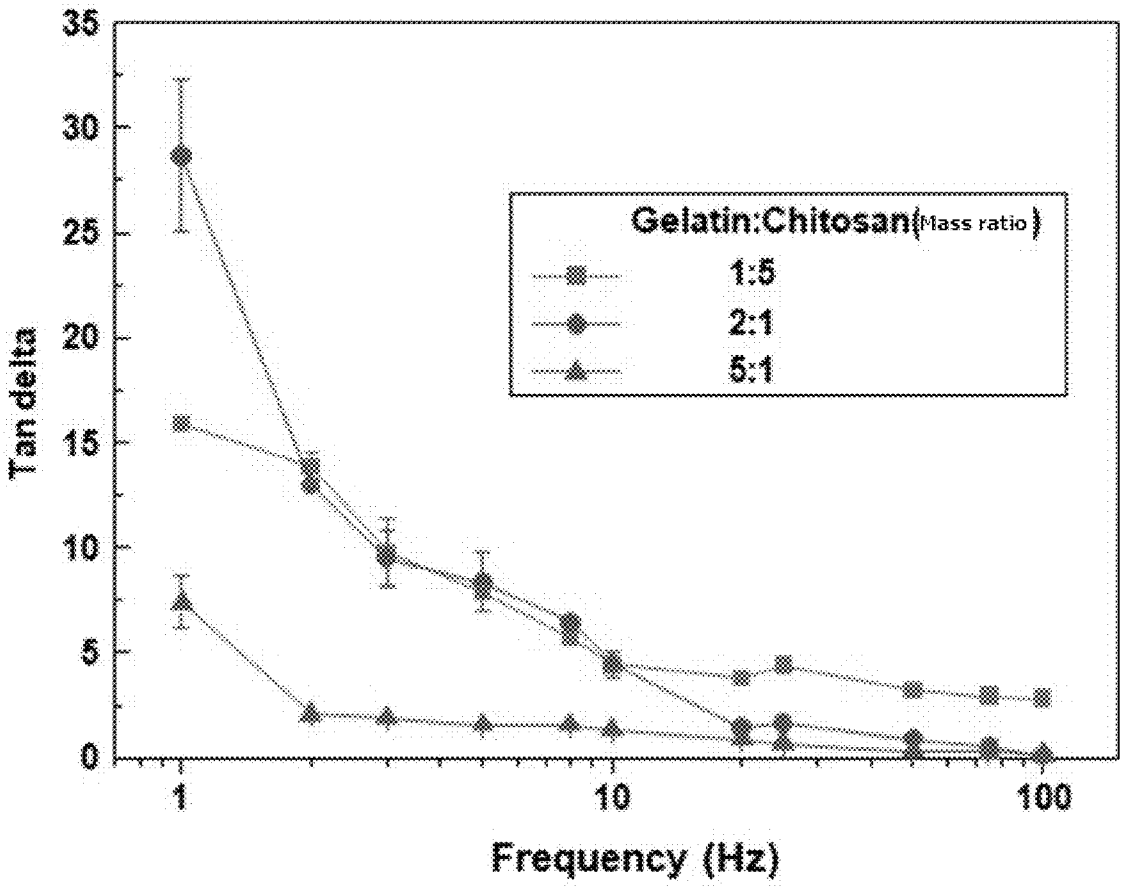
FIGS. 3A-3B show selectivity values of Examples 1 to 3 of the present disclosure.
Figure 3B:
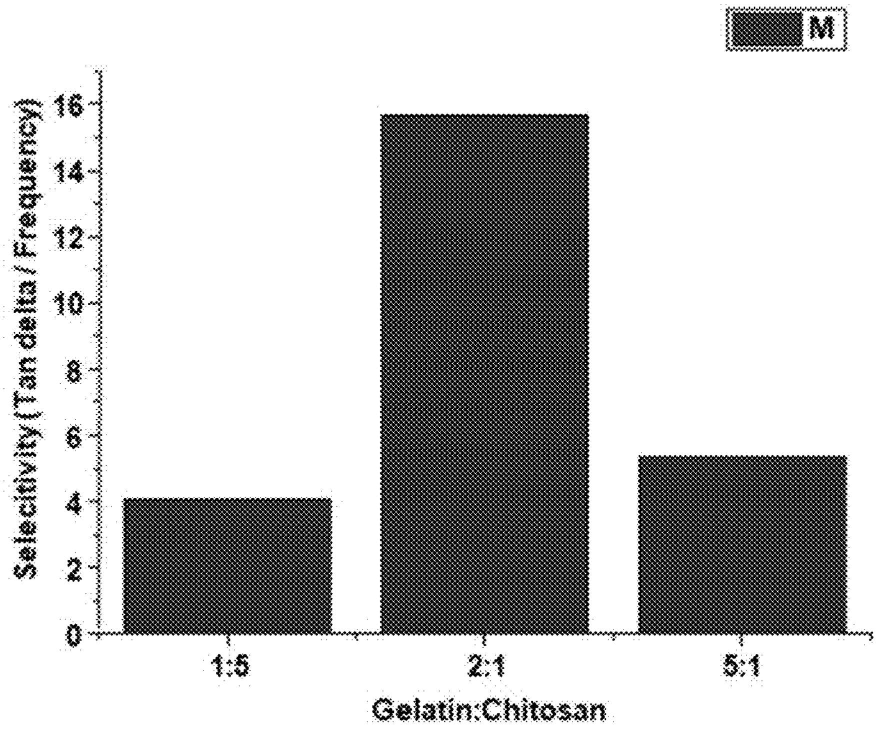

FIGS. 3A and 3B exhibit the selectivity values of Examples 1 to 3 of the present disclosure. The selectivity value varies depending on the composition ratio of chitosan and gelatin as two components of the hydrogel according to the present disclosure. In this regard, when gelatin is contained in an amount of 20 to 500 parts by weight based on 100 parts by weight of chitosan, a very high selectivity value which is 4 or greater is achieved.

The vibration sensor was placed on the hydrogel of Example 1. Then, the physical vibrations of 400 Hz and 50 Hz were applied thereto at 50 degrees C. temperature. Then, it was checked whether selective sound absorption was achieved. The result may be identified with reference to FIG.

Figure 4:
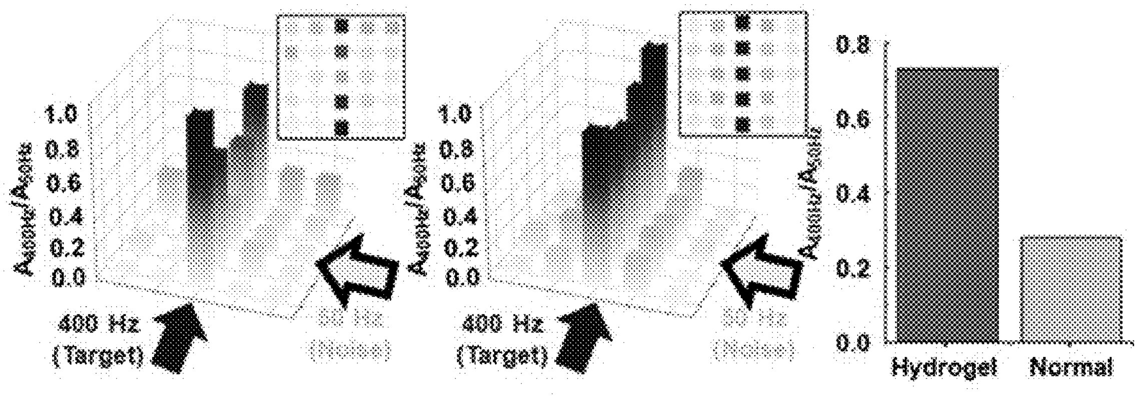
FIG. 4 shows a signal-to-noise ratio result when a vibration sensor is placed on the hydrogel of Example 1 of the present disclosure and then hydrogel is subjected to physical vibrations of 400 Hz and 50 Hz.

4. It may be identified that the hydrogel of Example 1 (hydrogel in the right bar graph of FIG. 4) exhibits the signal-to-noise ratio which increases at least twice, compared to the PDMS sensor (Normal in the right bar graph of FIG. 4).

Figure 5A:
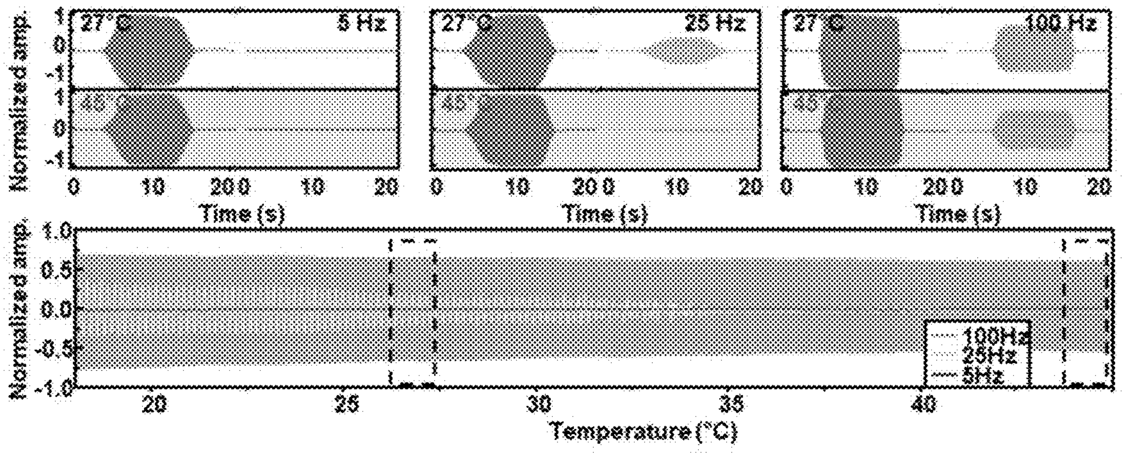
FIGS. 5A-5B show a result of measuring an amplitude value of a vibration passing through each of the hydrogel of Example 1 of the present disclosure and PDMS as a control.
Figure 5B:
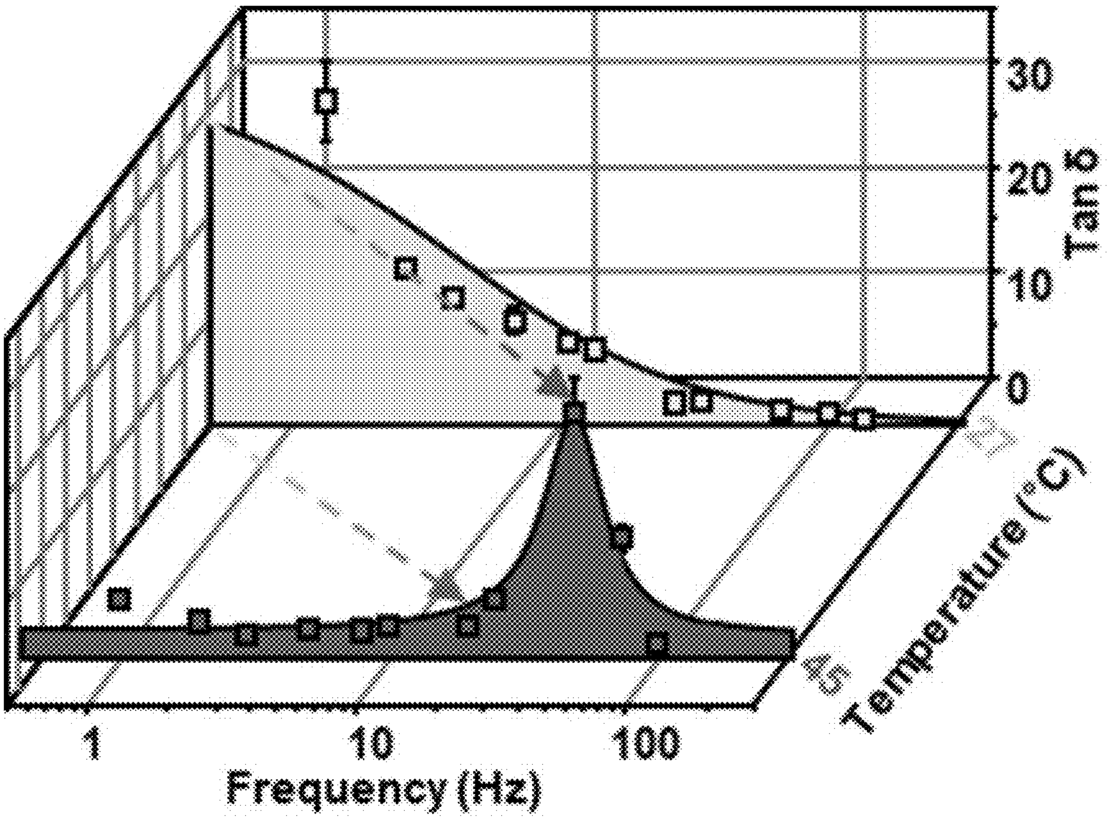

FIGS. 5A and 5B show a result of measuring an amplitude value of a vibration passing through each of the hydrogel of Example 1 of the present disclosure and PDMS as a control. In FIGS. 5A and 5B, the gray value is directed to the PDMS result, and the colored value is directed to the hydrogel result in accordance with the present disclosure. The PDMS did not damp the vibrations below 100 Hz regardless of the temperature. However, when using the material according to the present disclosure, the low frequency band of 5 Hz is damped at room temperature, and the frequency band of 25 Hz or lower is completely damped at 45 degrees C. or lower.

The damper in accordance with the present disclosure may be utilized as a sensor that selectively and directly measures a signal, or may be used as a damper together with another sensor as shown in FIGS. 5A and 5B. For example, the damper in accordance with the present disclosure may be utilized together with a conventional vibration sensor to measure signals such as sound waves, pulse, and heart rate in a living body. FIGS. 5A and 5B illustrate bio-signal measuring means in a form in which the hydrogel-based damper according to the present disclosure is stacked on one face or each of both opposing faces of a sensor (sensor in FIG. 6) capable of measuring vibration, etc.

Figure 6:
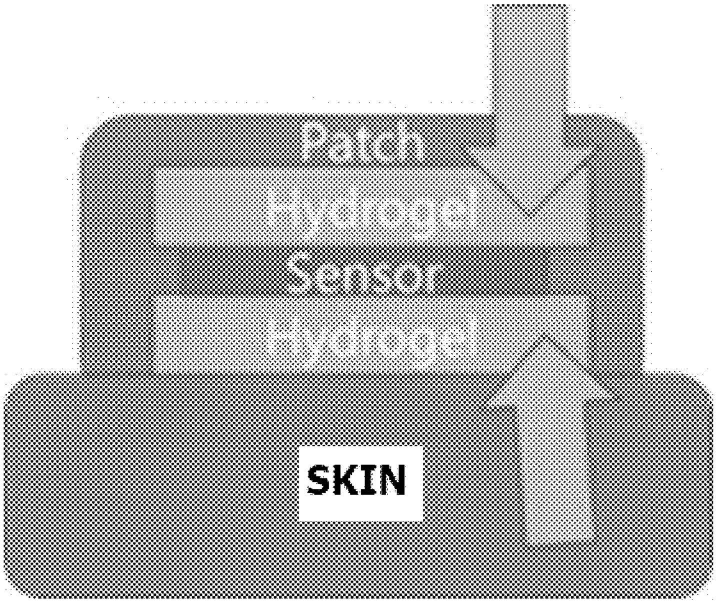
FIG. 6 illustrates a vibration measuring device for illustrating use of a damper in accordance with the present disclosure as a damper in conjunction with another vibration sensor.

In the signal measuring means exemplified in FIG. 6, the sensor may be a sensor based on an electrical signal, for example, a crack sensor as disclosed in Korean patent (10-2104944 and 10-2044152). Patent document 10-2104944 discloses a highly sensitive sensor comprising: a support; and a conductive thin metal film formed on at least one side of the support, wherein the conductive thin film includes cracks that are artificially formed according to an orientation direction, at least some of which have opposing surfaces in partial contact with each other, the crack surfaces undergo a variation in contact area or disconnection-reconnection events to cause a change in electrical resistance while moving relative to each other in response to external physical stimuli, and the sensor detects the resistance change to measure the external stimuli.

As described above, the present disclosure is described with reference to the drawings. However, the present disclosure is not limited to the embodiments and drawings disclosed in the present specification. It will be apparent that various modifications may be made thereto by those skilled in the art within the scope of the present disclosure. Furthermore, although the effect resulting from the features of the present disclosure has not been explicitly described in the description of the embodiments of the present disclosure, it is obvious that a predictable effect resulting from the features of the present disclosure should be recognized.

What is claimed is:

1. A frequency-selective signal damper comprising:
a viscous polymer exhibiting non-Newtonian fluid behavior; and
hydrogel exhibiting sol-gel phase transition.

2. The frequency-selective signal damper of claim 1, wherein the viscous polymer exhibits shear thinning in a damping region or a noise region,
wherein the hydrogel has a sol phase in the damping region or the noise region.

3. The frequency-selective signal damper of claim 1, wherein the viscous polymer has a Deborah number of 1 or lower in a damping region or a noise region.

4. The frequency-selective signal damper of claim 1, wherein the viscous polymer is gelatin, and the hydrogel is chitosan.

5. The frequency-selective signal damper of claim 1, wherein the signal is a physical or electromagnetic signal.

6. The frequency-selective signal damper of claim 4, wherein in a damping frequency band, the damper has a tangent delta value based on a frequency in a range of 4 or greater.

7. The frequency-selective signal damper of claim 6, wherein a content of the gelatin is in a range of 20 to 500 parts by weight based on 100 parts by weight of the chitosan.

8. The frequency-selective signal damper of claim 4, wherein the damper selectively damps a physical signal having a frequency below or equal to 50 Hz at a temperature below 50 degrees C.

9. An electrode for measuring a bio-signal comprising:
the frequency-selective signal damper of claim 1 disposed on an electrode configured to measure a bio-signal.

10. The electrode of claim 9, wherein the bio-signal includes a heart rate, brainwave, electrocardiogram, pulse or voice.

11. A signal discrimination sensor including the frequency-selective signal damper of claim 1:
disposed on a sensor configured to detect a signal.

12. The signal discrimination sensor of claim 11, wherein the signal discrimination sensor is a pass filter or a stop filter.

13. A vibration measuring device comprising:
a vibration measuring sensor having opposing faces; and
a frequency-selective signal damper stacked on one face or each of both opposing faces of the vibration measuring sensor,
wherein the frequency-selective signal damper comprises:
a viscous polymer exhibiting non-Newtonian fluid behavior; and
hydrogel exhibiting sol-gel phase transition.

14. The device of claim 13, wherein the vibration measuring sensor includes:
a support; and
a conductive thin metal film formed on at least one side of the support,
wherein the conductive thin film includes cracks that are artificially formed according to an orientation direction, at least some of which have opposing surfaces in partial contact with each other, the crack surfaces undergo a variation in contact area or disconnection-reconnection events to cause a change in electrical resistance while moving relative to each other in response to external physical stimuli, and the sensor detects the resistance change to measure the external stimuli.

15. The frequency-selective signal damper of claim 1, wherein the viscous polymer and the hydrogel are in a mixed solution of 5% by weight.

16. The frequency-selective signal damper of claim 1, wherein a damping band of the frequency-selective signal damper is selected to correspond to a noise frequency by controlling at least one of temperature, viscoelastic property, and diffusion coefficient of the hydrogel.

17. A method of frequency-selective signal damping comprising:
preparing the vibration measuring device of claim 13,
wherein the preparing further comprises selecting a damping band of the frequency-selective signal damper to correspond to a noise frequency by controlling at least one of temperature, viscoelastic property, and diffusion coefficient of the hydrogel; and
applying the composition to a substrate.

* * * * *